United States Patent [19]

Kaiser et al.

[11] Patent Number: 4,689,318
[45] Date of Patent: Aug. 25, 1987

[54] GRF ANALOGS

[75] Inventors: Emil T. Kaiser, New York, N.Y.; Gonul Velicelebi, San Diego, Calif.

[73] Assignee: The Salk Institute for Biological Studies, San Diego, Calif.

[21] Appl. No.: 770,683

[22] Filed: Aug. 29, 1985

[51] Int. Cl.$^4$ .................. A61K 37/43; C07K 7/10
[52] U.S. Cl. .................... 514/12; 530/324
[58] Field of Search .................. 530/324; 514/12

[56] References Cited

U.S. PATENT DOCUMENTS

| | | | |
|---|---|---|---|
| 4,514,331 | 4/1985 | Kaiser | 530/307 |
| 4,518,586 | 5/1985 | Rivier et al. | 514/12 |
| 4,528,190 | 7/1985 | Vale, Jr. et al. | 514/12 |
| 4,529,595 | 7/1985 | Rivier et al. | 514/12 |
| 4,595,676 | 6/1986 | Spiess et al. | 530/324 |

OTHER PUBLICATIONS

E. T. Kaiser and F. J. Kezdy, Science, vol. 223, pp. 249–225, 1/20/84 "Amphiphilic Secondary Structure: Design of Peptide Hormones".

*Primary Examiner*—Delbert R. Phillips
*Attorney, Agent, or Firm*—Fitch, Even, Tabin & Flannery

[57] ABSTRACT

Human pancreatic GRF and the hypothalamic GRFs for the human and several other mammalian species were earlier characterized and synthesized. The invention provides synthetic peptides which are potent stimulators of the release of pituitary GH in animals, including humans, and which have the formula: $R_1$-$R_2$$R_3$-Ala-$R_5$-$R_6$-$R_7$-$R_8$-$R_9$-$R_{10}$-$R_{11}$-$R_{12}$-$R_{13}$-Leu-$R_{15}$-Gln-Leu-$R_{18}$-$R_{19}$-$R_{20}$-$R_{21}$-Leu-Leu-Gln-Glu-$R_{26}$-$R_{27}$-$R_{28}$-Arg-Y wherein $R_1$ is Tyr, D-Tyr, Met, Phe, D-Phe, Leu, His or D-His, which has either a $C^a$Me or $N^a$Me substitution or is unsubstituted; $R_2$ is Ala or D-Ala; $R_3$ is Asp or D-Asp; $R_5$ is Ile or Leu; $R_6$ is Phe or Tyr; $R_7$ is Ser or Thr; $R_8$ is Ser, Asn, Thr or Gln; $R_9$ is Ala or Ser; $R_{10}$ is Tyr, Phe or Leu; $R_{11}$ in Arg, Orn or Lys; $R_{12}$ is Arg, Orn or Lys; $R_{13}$ is Ile, Leu, Phe or Val; $R_{15}$ is Gly or Ala; $R_{18}$ is Ala or Ser; $R_{19}$ is Ser or Ala; $R_{20}$ is Arg, Orn or Lys; $R_{21}$ is Arg, Orn or Lys; $R_{26}$ is Leu, Ile, Val or Phe; $R_{27}$ is Nle, Nva or a natural amino acid; $R_{28}$ is Ala, Leu, Asn, Gln, or Ser; and Y is OH or $NH_2$; provided however that at least four of the residues constituting $R_5$, $R_6$, $R_7$, $R_8$, $R_9$, $R_{10}$, $R_{11}$, $R_{12}$, $R_{13}$, $R_{15}$, $R_{18}$, $R_{19}$, $R_{20}$, $R_{21}$ and $R_{26}$ are different from the residues appearing in that respective position in the native molecule. These peptides as well as nontoxic salts thereof may be administered to animals, including humans and cold-booded animals, to stimulate the release of GH and may be used diagnostically.

20 Claims, No Drawings

GRF ANALOGS

The present invention relates to peptides having influence on the function of the pituitary gland in humans and other animals. In particular, the present invention is directed to peptides which promote the release of growth hormone by the pituitary gland.

BACKGROUND OF THE INVENTION

Physiologists have long recognized that the hypothalamus controls the secretory functions of the adenohypophysis with the hypothalamus producing special substances which stimulate or inhibit the secretion of each pituitary hormone. In 1982, human pancreatic (tumor) releasing factors (hpGRF) were isolated from extracts of human pancreatic tumors, purified, characterized, synthesized and tested, which were found to promote the release of GH by the pituitary. Since then, corresponding hypothalamic GH releasing factors from other species and from the human species have also been characterized and synthesized. Human hypothalamic GRF(hGRF) has been found to have the same formula as hpGRF, namely: H-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-Gln-Gln-Gly-Glu-Ser-Asn-Gln-Glu-Arg-Gly-Ala-Arg-Ala-Arg-Leu-NH$_2$.

SUMMARY OF THE INVENTION

Synthetic polypeptides which are analogs of human GRF have now been synthesized and tested which release GH from cultured pituitary cells. These peptides have at least four differences from the residues appearing in the native hormone between the 5-position and the 26-position. The peptides may also have a residue in the 1-position selected from Tyr, D-Tyr, Met, Phe, D-Phe, Leu, His and D-His (which residue may optionally have a methyl substitution either on the alpha-carbon or in the alpha amino group). The peptides may optionally have D-Ala at the 2-position and/or D-Asp at the 3-position. The peptides preferably also have a substitution such as Leu, Nle or Nva for Met in the 27-position.

Pharmaceutical compositions in accordance with the invention include such analogs which are about 29 residues in length, or a nontoxic salt of any of these, dispersed in a pharmaceutically or veterinarily acceptable liquid or solid carrier. Such pharmaceutical compositions can be used in clinical medicine, both human and veterinary, for administration for therapeutic purposes, and also diagnostically.

DETAILED DESCRIPTION OF PREFERRED EMBODIMENTS

The nomenclature used to define the peptides is that specified by Schroder & Lubke, "The Peptides", Academic Press (1965), wherein in accordance with conventional representation the amino group at the N-terminus appears to the left and the carboxyl group at the C-terminus to the right. By natural amino acid is meant one of common, naturally occurring amino acids found in proteins comprising Gly, Ala, Val, Leu, Ile, Ser, Thr, Lys, Arg, Asp, Asn, Glu, Gln, Cys, Met, Phe, Tyr, Pro, Trp and His. By Nle is meant norleucine, and by Nva is meant norvaline. Where the amino acid residue has isomeric forms, it is the L-form of the amino acid that is represented unless otherwise expressly indicated.

The invention provides synthetic peptides having the following sequence: $R_1$-$R_2$-$R_3$-Ala-$R_5$-$R_6$-$R_7$-$R_8$-$R_9$-$R_{10}$-$R_{11}$-$R_{12}$-$R_{13}$-Leu-$R_{15}$-Gln-Leu-$R_{18}$-$R_{19}$-$R_{20}$-$R_{21}$-Leu-Leu-Gln-Glu-$R_{26}$-R hd 27-$R_{28}$-Arg-Y wherein $R_1$ is Tyr, D-Tyr, Met, Phe, D-Phe, Leu, His or D-His, which has either a C$^a$Me or N$^a$Me substitution or is unsubstituted; $R_2$ is Ala or D-Ala; $R_3$ is Asp or D-Asp; $R_5$ is Ile or Leu; $R_6$ is Phe or Tyr; $R_7$ is Ser or Thr; $R_8$ is Ser, Asn, Thr or Gln; $R_9$ is Ala or Ser; $R_{10}$ is Tyr, Phe or Leu; $R_{11}$ is Arg, Orn or Lys; $R_{12}$ is Arg, Orn or Lys; $R_{13}$ is Ile, Leu, Phe or Val; $R_{15}$ is Gly or Ala; $R_{18}$ is Ala or Ser; $R_{19}$ is Ser or Ala; $R_{20}$ is Arg, Orn or Lys; $R_{21}$ is Arg, Orn or Lys; $R_{26}$ is Leu, Ile, Val or Phe; $R_{27}$ is Nle, Nva or a natural amino acid; $R_{28}$ is Ala, Leu, Asn, Gln, or Ser; and Y is OH or NH$_2$ provided however that at least four of the residues constituting $R_5$, $R_6$, $R_7$, $R_8$, $R_9$, $R_{10}$, $R_{11}$, $R_{12}$, $R_{13}$, $R_{15}$, $R_{18}$, $R_{19}$, $R_{20}$, $R_{21}$ and $R_{26}$ are different from the residues appearing in that respective position in the native molecule. By replacing 4 or more residues, it is felt that a shortened analog can be created having increased biological potency, even without an amidated C-terminus.

The peptides can be synthesized by a suitable method, such as by exclusively solid-phase techniques, by partial solid-phase techniques, by fragment condensation or by classical solution couplings. The employment of recently developed recombinant DNA techniques may be used to prepare an entire analog or a portion of an analog containing only natural amino acid residues. For example, the techniques of exclusively solid-phase synthesis are set forth in the textbook "Solid-Phase Peptide Synthesis", Stewart & Young, Freeman & Co., San Francisco, 1969, and are exemplified by the disclosure of U.S. Pat. No. 4,105,603, issued Aug. 8, 1978 to Vale et al. Classical solution synthesis is described in detail in the treatise "Methoden der Organischen Chemie (Houben-Weyl): Synthese von Peptiden", E. Wunsch (editor) (1974) Georg Thieme Verlag, Stuttgart, W. Ger. The fragment condensation method of synthesis is exemplified in U.S. Pat. No. 3,972,859 (Aug. 3, 1976). Other available syntheses are exemplified by U.S. Pat. Nos. 3,842,067 (Oct. 15, 1974) and 3,862,925 (Jan. 28, 1975).

Common to such chemical syntheses is the protection of the labile side chain groups of the various amino acid moieties with suitable protecting groups which will prevent a chemical reaction from occurring at that site until the group is ultimately removed. Usually also common is the protection of an alpha-amino group on an amino acid or a fragment while that entity reacts at the carboxyl group, followed by the selective removal of the alpha-amino protecting group to allow subsequent reaction to take place at that location. Accordingly, it is common that, as a step in the synthesis, an intermediate compound is produced which includes each of the amino acid residues located in its desired sequence in the peptide chain with side-chain protecting groups linked to the appropriate residues.

Also considered to be within the scope of the present invention are intermediates of the formula: $X^1R_1$(X or $X^2$)-$R_2$-$R_3$($X^3$)-Ala-$R_5$-$R_6$($X^2$)-$R_7$($X^4$)-$R_8$($X^4$ or $X^5$)-$R_9$($X^4$)-$R_{10}$($X^2$)-$R_{11}$($X^6$ or $X^7$)-$R_{12}$($X^6$ or $X^7$)-$R_{13}$-Leu-$R_{15}$-Gln($X^5$)-Leu-$R_{18}$($X^2$)-$R_{19}$($X^4$)-$R_{20}$($X^6$ or $X^7$)-$R_{21}$($X^7$)-Leu-Leu-Gln($X^5$)-Glu($X^3$)-$R_{26}$-$R_{27}$-$R_{28}$($X^4$ or $X^5$)-Arg($X^6$)-$X^9$ wherein: $X^1$ is either hydrogen or an a-amino protecting group. The a-amino protecting groups contemplated by $X^1$ are those well known to be useful in the art of step-wise synthesis of polypeptides.

Among the classes of a-amino protecting groups which may be employed as $X^1$ are (1) aromatic urethan-type protecting groups, such as fluorenylmethyloxycarbonyl (FMOC), benzyloxycarbonyl(Z) and substituted Z, such as p-chlorobenzyloxycarbonyl, p-nitrobenzyloxycarbonyl, p-bromobenzyloxycarbonyl, and p-methoxybenzyloxycarbonyl; (2) aliphatic urethan protecting groups, such as t-butyloxycarbonyl (BOC), diisopropylmethyloxycarbonyl, isopropyloxycarbonyl, ethoxycarbonyl, allyloxycarbonyl; and (3) cycloalkyl urethan-type protecting groups, such as cyclopentyloxycarbonyl, adamantyloxycarbonyl, and cyclohexyloxycarbonyl. The preferred a-amino protecting group is BOC, even when an $N^a$Me-substituted residue is employed in the 1-position.

X is hydrogen or a protecting group for the imidazole nitrogen of His, such as Tos.

$X^2$ may be a suitable protecting group for the phenolic hydroxyl group of Tyr, such as tetrahydropyranyl, tert-butyl, trityl, Bzl, CBZ, 4Br-CBZ and 2,6-dichlorobenzyl(DCB). The preferred protecting group is 2,6-dichlorobenzyl. $X^2$ can be hydrogen which means that there is no side-chain protecting group on the amino acid residue in that position.

$X^3$ is hydrogen or a suitable ester-forming protecting group for the carboxyl group of Asp or Glu, such as benzyl(OBzl), 2,6-dichlorobenzyl, methyl and ethyl.

$X^4$ may be a suitable protecting group for the hydroxyl group of Thr or Ser, such as acetyl, benzoyl, tert-butyl, trityl, tetrahydropyranyl, Bzl, 2,6-dichlorobenzyl and CBZ. The preferred protecting group is Bzl. $X^4$ can be hydrogen, which means there is no protecting group on the hydroxyl group.

$X^5$ is hydrogen or a suitable protecting group for the side chain amido group of Asn or Gln. It is preferably xanthyl(Xan).

$X^6$ is a suitable protecting group for the guanidino group of Arg, such as nitro, Tos, CBZ, adamantyloxycarbonyl, and BOC, or is hydrogen.

$X^7$ is hydrogen or a suitable protecting group for the side chain amino group of Lys or Orn. Illustrative of suitable side chain amino protecting groups are 2-chlorobenzyloxycarbonyl(2-Cl-Z), Tos, t-amyloxycarbonyl and BOC.

$X^8$ is hydrogen or a suitable side-chain protecting group as generally specified above.

Met can optionally be protected by oxygen, but is preferably left unprotected.

The selection of a side chain amino protecting group is not critical except that generally one is chosen which is not removed during deprotection of the a-amino groups during the synthesis. However, for some amino acids, e.g. His, protection is not generally necessary after coupling is completed, and the protecting groups may be the same.

$X^9$ is a suitable protecting group for the C-terminal carboxyl group or is an anchoring bond used in solid-phase synthesis for linking to a solid resin support, or is des-$X^9$, in which case the Arg residue at the C-terminus is amidated. When such a solid resin support is used, it is broadly considered to be a protecting group, and an appropriate one, as known in the art is chosen, such as: —O—CH$_2$-resin support, —NH-benzhydrylamine (BHA) resin support or —NH-paramethylbenzhydrylamine (MBHA) resin support. When the unsubstituted amide is desired at the C-terminus, use of BHA or MBHA resin is preferred, because cleavage directly gives the amide.

In the formula for the intermediate, at least one of the X-groups is a protecting group or $X^9$ includes resin support. Thus, the invention also provides a method for manufacturing a peptide of interest by (a) forming a peptide intermediate having at least one protective group and the formula (II): $X^1$-$R_1$(X or $X^2$)-$R_2$-$R_3$($X^3$)-Ala-$R_5$-$R_6$($X^2$)-$R_7$($X^4$)-$R_8$($X^4$ or $X^5$)-$R_9$($X^4$)-$R_{10}$($X^2$)-$R_{11}$($X^6$ or $X^7$)-$R_{12}$($X^6$ or $X^7$)-$R_{13}$ -Leu-$R_{15}$-Gln($X^5$)-Leu-$R_{18}$($X^2$)-$R_{19}$($X^4$)-$R_{20}$($X^6$ or $X^7$)-$R_{21}$($X^7$)-Leu-Leu-Gln($X^5$)-Glu($X^3$)-$R_{26}$-$R_{27}$-$R_{28}$($X^4$ or $X^5$)-Arg($X^6$)-$X^9$ wherein: X, $X^1$, $X^2$, $X^3$, $X^4$, $X^5$, $X^6$, $X^7$ and $X^8$ are each either hydrogen or a protective group and $X^9$ is either a protective group or an anchoring bond to resin support or des-$X^9$; (b) splitting off the protective group or groups or anchoring bond from said peptide of the formula (II); and (c) if desired, converting a resulting peptide into a nontoxic salt thereof.

In selecting a particular side chain protecting group to be used in the synthesis of the peptides, the following general rules are followed: (a) the protecting group preferably retains its protecting properties and is not split off under coupling conditions, (b) the protecting group should be stable to the reagent and, with the exception of Xan, is preferably stable under the reaction conditions selected for removing the a-amino protecting group at each step of the synthesis, and (c) the side chain protecting group must be removable, upon the completion of the synthesis containing the desired amino acid sequence, under reaction conditions that will not undesirably alter the peptide chain.

Compounds of this invention can also be prepared via recombinant DNA methodology. In their preparation, a nucleotide sequence coding for the desired peptide is prepared using now routine methods for such synthesis. These methods generally involve preparation of oligonucleotides coding both for fragments of the desired coding sequence and for the complementary sequence thereof. The oligonucleotides are designed to provide overlap of one fragment of the coding sequence with two fragments of the complementary sequence and vice versa. The oligonucleotides are paired and joined, ultimately producing the desired gene sequence.

The sequence is inserted into a cloning vector at a location which permits the peptide product for which it codes to be expressed. A suitable cloning vector contains at least a portion of a gene's expression control sequence.

A typical expression control sequence can be described in terms of five elements. In the order in which they appear in the gene, the elements are as follows:
(a) the promoter region;
(b) the 5' untranslated region;
(c) the protein coding sequence;
(d) the 3' untranslated region; and
(e) the transcription termination site.

The function of each of these elements in gene systems is well recognized. The promoter region mediates initiation of messenger RNA (mRNA) production (transcription). The promoter may be (1) free of external control (constitutive), (2) under the control of a repressor, a substance that, when present, represses gene function, or (3) under the control of an inducer, a substance that is required to induce gene function. An outer membrane lipoprotein (lpp) gene from *E coli*, for example, is free from external control and thus is termed "constitutive".

Located at or near the promoter is the "transcription initiation site", a point at which RNA polymerase initiates transcription of mRNA. Once transcription is initiated, mRNA is produced. The structure of the resulting mRNA is determined by the DNA sequences of the gene elements (b) to (d) above.

The resulting mRNA carries a sequence which is translatable into protein product. The translatable sequence is located downstream from the 5' untranslated region and upstream from the 3' untranslated region. Translation is mediated by the binding of ribosomes to a sequence in the mRNA 5' untranslated region denoted as the ribosome binding site and is initiated at the translation start codon (AUG) appearing as the first codon of the product gene sequence and coding as well for the amino acid methionine (Met). Translation terminates at one or more termination codons appearing at the end of the translation region.

By the techniques of recombinant DNA, it has become possible to prepare cloning vectors useful for the production of selected foreign (exogenous) proteins by inserting into such vectors an expression control sequence, i.e., a sequence of nucleotides that controls and regulates expression of structural genes with production of exogenous protein when operatively linked to those genes.

In the context of the foregoing, the term "expression control sequence" includes elements (a), (b), (d) and (e) above.

Recombinant DNA methodology can be employed to express compounds of this invention either as a portion of a larger "hybrid" molecule or by direct expression. In the direct expression mode, the cloning vector is designed such that the expression product is composed entirely of desired product preceded by a methionine (Met) residue resulting from the presence of the essential start codon. The superfluous Met residue can be removed by treating the product with cyanogen bromide or with phenyl isothiocyanate followed by a strong anhydrous acid, such as trifluoroacetic acid.

In the hybrid molecule expression mode, a DNA sequence coding for the desired product is inserted into the expression control sequence of a cloning vector at a point such that the product expressed comprises a hybrid protein. By "hybrid protein" as used herein is meant a recombinant DNA product comprising a foreign protein, generally all or a portion of the natural (endogenous) protein produced by the expression control sequence (for example, lipoprotein in the lipoprotein gene), to which is attached the desired protein.

The properly designed hybrid protein produced by recombinant DNA methodology will contain a cleavage site at the junction of the endogenous protein portion and the desired product. The cleavage site permits generation of mature product by chemical or enzymatic treatment of the hybrid protein product. Highly useful selective cleavage sites comprise a DNA sequence which codes for an amino acid or a sequence of amino acids which can be cleaved chemically or enzymatically at its C-terminus.

Examples of chemical agents useful for cleaving proteins are cyanogen bromide, BNPS-skatole, hydroxylamine, and the like. Cyanogen bromide cleaves proteins at the C-terminus of a methionine residue. Therefore, the selective cleavage site is at a methionine residue itself.

Hydroxylamine cleaves at the C-terminus of the moiety-Asn-Q in which Q is Gly, Leu, or Ala.

BNPS-skatole cleaves at the C-terminus of a tryptophan residue.

Examples of enzymatic agents useful for cleavage are trypsin, papain, pepsin, plasmin, thrombin, enterokinase, and the like. Each effects cleavage at a particular amino acid sequence which it recognizes.

An enzyme of choice is enterokinase. Therefore, a preferred selective cleavage site is that which enterokinase recognizes, viz., a DNA sequence coding for the amino acid sequence -(Asp)$_n$-Lys- in which n is an integer from 2 to 4.

The most preferred selective cleavage site, because the compounds of this invention preferably lack methionine, is a methionine residue. This residue, joined to the N-terminus of the desired product, is readily cleaved by known methods using cyanogen bromide to produce the desired mature product.

Certain eukaryotic cells, e.g. yeast and mammalian cells, are capable of producing small peptides by synthesizing a larger precursor molecule. These organisms contain highly specific enzymes which are capable of separating the desired peptide from its precursor at well defined cleavage sites. Paired basic amino acid residues are among the most well defined proteolytic processing sites. Another example of such processing sites are the amino acids Glu-Ala or Asp-Ala. Most hypothalamic peptides, as well as some pituitary peptides, are produced in this fashion. Other examples of small peptide production in eukaryotic organisms are yeast alpha-factor or a-factor which are small peptide mating pheromones.

It should be possible to attach DNA sequences encoding synthetic GRF analogs to the precursor portion of such protein-encoding sequences (often called the pre-pro segment), immediately adjacent to and downstream of their normal proteolytic processing sites. Cultures of eukaryotic cells bearing plasmid elements comprised of such an expression unit should be able to produce the desired precursor-peptide molecule using the normal mechanisms of gene expression of the host cells. Furthermore, the normal cellular processes should provide for the precise removal of the desired product from the precursor molecule.

In constructing useful cloning vectors, several elements are required. Two of the required elements are common to all useful cloning vectors. First, the vector must have a DNA segment containing a functional origin of replication (replicon). Plasmids and phage DNA by their very nature contain replicons facilitating replication in a host cell.

Secondly, the vector must have a DNA segment which conveys to a transformable host cell a property useful for selection of transformed cells from non-transformed cells. Any of a wide range of properties can be used for selection purposes. One of the most commonly used properties is antibiotic resistance, e.g., tetracycline resistance or ampicillin resistance, particularly, in the transformation of E. coli. Complementation of auxotrophic mutants by plasmid-borne copies of the wild type gene capable of curing such deficiencies is also commonly used.

The foregoing two elements generally are present in readily available and recognized cloning vectors. Examples of suitable cloning vectors are bacterial plasmids, such as plasmids from E. coli, including pBR322, pMB9, ColEl, pCRl; wider host range plasmids, including RP4; phage DNAs, such as lambda, and the like. Most, if not all, of the above-recognized vectors already carry the aforedescribed two elements.

A third element is the expression control sequence. Any of a wide range of such control sequences can be used including, for example, those from the lipoprotein gene, the β-galactosidase gene, the tryptophan gene, the β-lactamase gene, phage lambda, and the like.

In producing a suitable cloning vector by insertion of the selected expression control sequence, routine methods are used. Various sites exist within cloning vectors at which cuts can be made using a restriction endonuclease specific for such site. Any of these sites can be selected for insertion of the expression control sequence. As an example, in the well-recognized and documented plasmid pBR322, several suitable restriction sites exist, any of which may be employed as insertion sites. A PstI site is located within the gene for β-lactamase. Other sites outside of any specific coding region are EcoRI and PvuII. These and other sites are well recognized by those skilled in the art.

Taking advantage of any of these sites or others, insertion of an expression control sequence or the essential portion thereof can be readily accomplished in production of vectors defined by this invention.

A fourth element, of course, is the DNA sequence coding for the desired product. As previously noted, this DNA sequence is constructed synthetically by using the recognized phosphotriester method or some other well-recognized method.

Suitable cloning vectors can be used in a wide range of host organisms, for example, gram-negative prokaryotic organisms, such as *Escherichia coli*, Serratia, Pseudomonas and the like; gram-positive prokaryotic organisms, such as Bacillus, Streptomyces and the like; and eukaryotic organisms, such as Saccharomyces and the like. When the host organism is a gram-negative prokaryotic organism, *E. coli* is preferred, for example, a *E. coli* K-12 strain, such as RV308.

Employing well recognized methodology, the appropriately prepared cloning vectors are used to transform suitable host organisms, are amplified in such organisms, and exogenous protein product is expressed using standard fermentation conditions. The exogenous protein product is isolated by routine methods from the resulting fermentation broth.

A typical procedure for product isolation from a Met cleavage site-containing precursor involves lyophilizing the product-containing cells. To one liter of 70% v/v formic acid is added 10 grams of lyophilized fermentation solids. After dissolution (about 60 minutes), the solution is adjusted in cyanogen bromide concentration to 0.1 M by the addition of 10.6 grams of reagent. Quantitative peptide cleavage to the desired amino-terminal product is complete in about 8 hours at 23° C. Formic acid is removed by evaporation under vacuum, and the cleaved fermentation solids are lyophilized. The solids are dissolved at 10 grams liter in 10% v/v acetic acid and applied to 5% of the column volume of a G-50 superfine Sephadex column (2.6×100 cm) flowing at a rate of 5 cm/hour, 4° C. Purification to homogeneity is achieved by reverse phase on a 0.46× $\cong$ cm Zorbax $C_8$ column, employing a linear gradient of acetonitrile in 0.1 M ammonium phosphate, pH 7.2. The desired product is desalted on Sephadex G-25 in 0.01 M ammonium bicarbonate, pH 8.5, and lyophilized.

When peptides are not prepared using recombinant DNA technology, they are preferably prepared using solid phase synthesis, such as that generally described by Merrifield, *J. Am. Chem. Soc.*, 85, p. 2149 (1963), although other equivalent chemical syntheses known in the art can also be used as previously mentioned. Solid-phase synthesis is commenced from the C-terminal end of the peptide by coupling a protected a-amino acid to a suitable resin. Such a starting material can be prepared by attaching an a-amino-protected amino acid by an ester linkage to a chloromethylated resin or a hydroxymethyl resin, or by an amide bond to a BHA resin or MBHA resin. The preparation of the hydroxymethyl resin is described by Bodansky et al., *Chem. Ind.* (London) 38, 1597–98 (1966). Chloromethylated resins are commercially available from Bio Rad Laboratories, Richmond, California and from Lab. Systems, Inc. The preparation of such a resin is described by Stewart et al., "Solid Phase Peptide Synthesis" (Freeman & Co., San Francisco 1969), Chapter 1, pp. 1–6. BHA and MBHA resin supports are commercially available but are generally used only when the desired polypeptide being synthesized has an unsubstituted amide at the C-terminal.

The C-terminal amino acid, i.e. Arg, protected by BOC and by Tos, can be first coupled to a chloromethylated resin or to a BHA or MBHA resin as described hereinafter. Following the coupling of the BOC-protected amino acid to the resin support, the a-amino protecting group is removed, as by using trifluoroacetic acid (TFA) in methylene chloride or TFA alone. The deprotection is carried out at a temperature between about 0° C. and room temperature. Other standard cleaving reagents, such as HCl in dioxane, and conditions for removal of specific a-amino protecting groups may be used as described in Schroder & Lubke, "The Peptides", 1, pp. 72–75 (Academic Press 1965).

After removal of the a-amino protecting group, the remaining a-amino- and side chain-protected amino acids are coupled step-wise in the desired order to obtain the intermediate compound defined hereinbefore, or as an alternative to adding each amino acid separately in the synthesis, some of them may be coupled to one another prior to addition to the solid phase reactor. The selection of an appropriate coupling reagent is within the skill of the art. Particularly suitable as a coupling reagent is N,N'-dicyclohexyl carbodiimide (DCCI).

The activating reagents used in the solid phase synthesis of the peptides are well known in the peptide art. Examples of suitable activating reagents are carbodiimides, such as N,N'-diisopropylcarbodiimide and N-ethyl-N'-(3-dimethylaminopropyl)carbodiimide. Other activating reagents and their use in peptide coupling are described by Schroder & Lubke supra, in Chapter III and by Kapoor, *J. Phar. Sci.*, 59, pp. 1–27 (1970).

Each protected amino acid or amino acid sequence is introduced into the solid phase reactor in about a four-fold or more excess, and the coupling may be carried out in a medium of dimethylformamide(DMF): $CH_2Cl_2$ (1:1) or in DMF or $CH_2Cl_2$ alone. In cases where incomplete coupling occurs, the coupling procedure is repeated before removal of the a-amino protecting group prior to the coupling of the next amino acid. The success of the coupling reaction at each stage of the synthesis, if performed manually, is preferably monitored by the ninhydrin reaction, as described by E. Kaiser et al., *Anal. Biochem.* 34, 595 (1970). The coupling reactions can be performed automatically, as on a Beckman 990 automatic synthesizer, using a program such as that reported in Rivier et al. *Biopolymers*, 1978, 17, pp. 1927–1938.

After the desired amino acid sequence has been completed, the intermediate peptide can be removed from the resin support by treatment with a reagent, such as liquid hydrogen fluoride, which not only cleaves the peptide from the resin but also cleaves all remaining side chain protecting groups X, $X^2$, $X^3$, $X^4$, $X^5$, $X^6$, $X^7$ and $X^8$ and also the a-amino protecting group $X^1$ if one is used, to obtain the amidated peptide. Should Met be present in the sequence, the BOC protecting group is preferably first removed using trifluoroacetic acid(TFA)/ethanedithiol prior to cleaving the peptide from the resin with HF to eliminate potential S-alkylation. When using hydrogen fluoride for cleaving, anisole and methylethyl sulfide are included as scavengers in the reaction vessel.

Example I sets forth a preferred method for synthesizing a preferred amidated peptide by the solid-phase technique. Synthesis of corresponding peptides varying in length can be effected in the same manner by merely adding or eliminating the requisite number of amino acids at either end of the chain; however, it is presently felt that biologically active analogs should contain the indicated sequence, or equivalents, from the N-terminus to residue 27.

EXAMPLE I

The synthesis of the peptide [$Ser^{7,8,19}$, $Ala^{9,15,18,28}$, $Arg^{12,21}$, $Leu^{13,26,27}$]-hGRF(1-29)-$NH_2$ having the formula: H-Tyr-Ala-Asp-Ala-Ile-Phe-Ser-Ser-Ala-Tyr-Arg-Arg-Leu-Leu-Ala-Gln-Leu-Ala-Ser-Arg-Arg-Leu-Leu-Gln-Glu-Leu-Leu-Ala-Arg-$NH_2$ is conducted in a stepwise manner using a Beckman 990 peptide synthesizer on a MBHA resin having a substitution range of about 0.35 to 0.5 mmoles/g. resin. Coupling of BOC-Arg(Tos) to the resin is performed by the general procedure set forth in U.S. Pat. No. 4,292,313 to Vale, using KF in DMF at about 60° C. for 24 hours with stirring, and it results in the substitution of about 0.35 mmol. Arg per gram of resin.

After deblocking and neutralization, the peptide chain is built step-by-step on the resin. Deblocking, neutralization and addition of each amino acid is performed in general accordance with the procedure set forth in detail in Rivier, J., *J. Amer. Chem. Soc.*, 96, 2986-2992 (1974). All solvents that are used are carefully degassed by sparging with an inert gas, e.g. helium or nitrogen, to insure the absence of oxygen.

Deblocking is preferably carried out in accordance with Schedule A which follows:

| | SCHEDULE A | |
|---|---|---|
| | Reagent | Mixing time (Min.) |
| 1. | 60% TFA/2% ethanedithiol | 10 |
| 2. | 60% TFA/2% ethanedithiol | 15 |
| 3. | IPA/1% ethanedithiol | 0.5 |
| 4. | $Et_3N$ (10%) in $CH_2Cl_2$ | 0.5 |
| 5. | MeOH | 0.5 |
| 6. | $Et_3N$ (10%) in $CH_2Cl_2$ | 0.5 |
| 7. | MeOH (twice) | 0.5 |
| 8. | $CH_2Cl_2$ (twice) | 0.5 |

The couplings are preferably carried out as set out in Schedule B which follows:

| | SCHEDULE B | |
|---|---|---|
| | Reagent | Mixing time (Min.) |
| 9. | DCCI | — |
| 10. | Boc—amino acid | 50-90 |
| 11. | MeOH (twice) | 0.5 |
| 12. | $CH_2Cl_2$ (twice) | 0.5 |
| 13. | $Ac_2O$ (3 M) in $CH_2Cl_2$ | 15.0 |
| 14. | $CH_2Cl_2$ | 0.5 |
| 15. | MeOH | 0.5 |
| 16. | $CH_2Cl_2$ (twice) | 0.5 |

Briefly, one to two mmol. of BOC-protected amino acid in methylene chloride is used per gram of resin, plus one equivalent of 1.0 molar DCCI in methylene chloride for two hours. When BOC-Arg(TOS) is being coupled, a mixture of 50% DMF and methylene chloride is used. Bzl ether is used as the hydroxyl side-chain protecting group for Ser and Thr. The amido group of Asn or Gln is protected by Xan when DCC coupling is used as is preferred. p-Nitrophenyl ester(ONp) may also be used to activate the carboxyl end of Asn or Gln, and for example, BOC-Asn(ONp) can be coupled overnight using one equivalent of HOBt in a 50% mixture of DMF and methylene chloride, in which case no DCC is added. 2-chloro-benzyloxycarbonyl(2Cl-Z) is used as the protecting group for the Lys side chain. Tos is used to protect the guanidino group of Arg and the imidazole nitrogen of His, and the Glu or Asp side-chain carboxyl group is protected with OBzl. The phenolic hydroxyl group of Tyr is protected with 2,6-dichlorobenzyl(DCB). At the end of the synthesis, the following composition is obtained: BOC-Tyr(X)-Ala-Asp($X^3$)-Ala-Ile-Phe-Ser($X^4$)-Ser($X^4$)-Ala-Tyr($X^2$)-Arg($X^6$)-Arg($X^6$)-Leu-Leu-Ala-Gln-($X^5$)-Leu-Ala-Ser($H^4$)-Arg($X^6$)-Arg($X^6$)-Leu-Leu-Gln($X^5$)-Glu($X^3$)-Leu-Leu-Ala-Arg($X^6$)-$X^9$ wherein X is Tos, $X^2$ is DCB, $X^3$ is OBzl, $X^4$ is Bzl, $X^5$ is Xan, $X^6$ is Tos, $X^7$ is 2ClZ and $X^9$ is —NH-resin support. Xan may have been partially or totally removed by TFA treatment used to deblock the a-amino protecting group.

In order to cleave and deprotect the protected peptide-resin, it is treated with 1.5 ml. anisole, 0.5 ml. methylethylsulfide and 15 ml. hydrogen fluoride(HF) per gram of peptide-resin, at −20° C. for one-half hour and at 0° C. for one-half hour. After elimination of the HF under high vacuum, the resin-peptide remainder is washed alternately with dry diethyl ether and chloroform, and the peptide is then extracted with degassed 2 N aqueous acetic acid and separated from the resin by filtration.

The cleaved and deprotected peptide is then dissolved in 0-5% acetic acid and subjected to purification which may include Sephadex G-50 fine gel filtration.

The peptide is then further purified by preparative or semi-preparative HPLC as described in Rivier et al., *Peptides: Structure and Biological Function*, (1979) pp. 125-8 and Marki et al. *J. Am. Chem. Soc.* 103, 3178 (1981). Cartridges fitting Waters Associates prep LC-500 are packed with 15–20 μ $C_{18}$ Silica from Vydac (300A). A gradient of $CH_3CN$ in TEAP is generated by a low pressure Eldex gradient maker, as described in Rivier, J., *J. Liq. Chromatography* 1, 343-367 (1978). The chromatographic fractions are carefully monitored by HPLC, and only the fractions showing substantial purity are pooled. Desalting of the purified fractions, independently checked for purity, is achieved using a gradient of $CH_3CN$ in 0.1% TFA. The center cut is then lyophilized to yield the desired peptide, the purity of which can be greater than 98%.

EXAMPLE II

The synthesis of a peptide having the same sequence but in free acid form, i.e. [Ser$^{7,8,19}$, Ala$^{9,15,18,28}$, Arg$^{12,21}$, Leu$^{13,26,27}$]-hGRF(1-29)-OH having the formula: H-Tyr-Ala-Asp-Ala-Ile-Phe-Ser-Ser-Ala-Tyr-Arg-Arg-Leu-Leu-Ala-Gln-Leu-Ala-Ser-Arg-Arg-Leu-Leu-Gln-Glu-Leu-Leu-Ala-Arg-OH is conducted in a stepwise manner using a Beckman 990 peptide synthesizer on a chloromethylated resin having a substitution range of about 0.35 to 0.5 mmoles/g. resin. Coupling of BOC-Arg(Tos) to the resin is performed by the general procedure set forth by Monahan et al. in *Biopolymers*, 12 (1973) pp. 2513-19, using methylene chloride as a solvent for 2 M hours with stirring plus one equivalent of 2 M DCCl in methylene chloride, and it results in the substitution of about 0.35 mmol. Arg per gram of resin. The remainder of the synthesis is carried out as in Example I, including the cleavage, deprotection and purification.

The peptide is judged to be substantially pure using TLC and HPLC.

EXAMPLE III

The synthesis of the same peptide synthesized in Example II is carried out using recombinant DNA technology.

The 1.7 Kb EcoRI fragment encoding the alpha-factor structural gene, as described by Kurjan and Herskowitz (*Cell* 30:933-943, Oct. 1982), is subcloned into pBR322 such that the alpha-factor structural gene is in the same orientation as the tetracycline resistance gene. This plasmid is digested with BalI and reclosed; the resulting plasmid contains the alpha-factor promoter, pre-pro-peptide coding sequence and a portion of the 13 amino acid mature alpha-factor peptide. This plasmid is further modified by inserting a BamHI linker into the unique PvuII site of this vector, thus creating a site for insertion of the GRF analog encoding sequence.

The following nucleotide sequence (sense strand) is selected for the GRF analog described in Example II: TAT GCT GAC GCT ATT TTC TCC TCC GCC TAT AGA AGA CTT CTT GCT CAG CTT GCC TCC AGA AGA CTC CTC CAA GAA CTT CTT GCT AGG TAG and includes the TAG terminator code at its 3'-end. This DNA sequence, along with its antisense strand, is synthesized using state-of-the-art techniques. In order to render this sequence compatible with the expression vector, the following sequence, which codes for a portion of the alpha-factor peptide and processing, sites, is added to the 5'-end of the sense strand of the GRF analog: CCAACCAATG-TACAAAAGG. The antisense strand is comprised of the exact complement to both this oligo and the GRF analog, but it contains a BamHI overhang on its 5'-end.

The vector, prepared as described above, is then cut with BamHI and BalI and the synthetic gene is inserted, creating a vector with the following features. It contains the alpha-factor promoter and pre-pro-sequence, as well as one alpha-factor peptide-encoding sequence. This peptide-encoding sequence is followed by the sequence for Lys-Arg, which signals proteolytic cleavage of the GRF analog from the alpha-factor peptide. The GRF analog, containing the translation stop, is located after the Lys-Arg sequence.

The GRF analog expression unit is precisely excised from this vector by digestion with BamHI and BglII and the fragment is isolated from a 6% acrylamide gel by electroelution, and phenol-extracted and ethanol-precipitated. Approximately 20 ng of this fragment is ligated, under standard conditions, to 6 ng of a dephosphorylated BamHI digest of a suitable yeast shuttle vector, preferably one based upon pBR322 into which yeast-specific sequences have been inserted, e.g. the expression vector TRP209 which is described in detail in U.S. patent application Ser. No. 747,152 filed June 20, 1985 by Thill et al., the disclosure of which is incorporated herein by reference. It is then used to transform *E. coli* strain MC1061 to ampicillin-resistance. Transformants are analyzed by XbaI digestion of minilysates. Those with the correct orientation, i.e., the 3'-end of the gene next to the transcription terminator, are chosen by identification of diagnostic restriction fragments relative to standards of known molecular weight. The resulting yeast expression vector carries the wild type TRP1 gene for selection in yeast and the origin of replication from the endogenous yeast plasmid 2μ circle. It is used to transform a tryptophan-requiring Saccharomyces strain, such as GG1OO-14D (ATCC #20762), to prototrophy. Additionally, it bears the expression cassette containing the previously described alpha-factor promoter, pre-pro-region, alpha-factor peptide, processing sites, GRF analog and alpha-factor transcription terminator.

Positive transformants are generated using standard techniques and are grown in tryptophan-deficient synthetic media in batch or continuous culture. Immunoreactive GRF analogs are detected in the growth media via RIA. Analysis shows that the 29-amino acid peptide having free acid at the C-terminus is produced.

EXAMPLE IV

The solid-phase syntheses of the following hGRF analogs are carried using the methods as generally taught in Examples I and II:

[His$^1$, Ser$^{7,8,19}$, Ala$^{9,15,18,28}$, Arg$^{12,21}$, Leu$^{13,26,27}$]-hGRF(1-29)-NH$_2$;

[His$^1$, Ser$^{7,8}$, Ala$^{9,15,18,28}$, Arg$^{12,21}$, Leu$^{13,26}$Ala$^{27}$]-hGRF(1-29)-NH$_2$;

[His$^1$, Ser$^{8,19}$, Ala$^{9,15,18,28}$, Arg$^{12,21}$, Leu$^{13,26,27}$]-hGRF(1-29)-NH$_2$;

[Ser$^{7,19}$, Gln$^8$, Ala$^{9,15,18,28}$, Arg$^{12,21}$, Leu$^{13,26,27}$]-hGRF(1-29)-NH$_2$;

[Phe$^1$, Leu$^{5,13,26,27}$, Ser$^{7,8,19}$, Ala$^{15,18,28}$, Arg$^{12,21}$]-hGRF(1-29)-NH$_2$;

[Ser$^{7,8,19,28}$, Ala$^{9,15,18}$, Phe$^{10}$, Arg$^{12,21}$, Leu$^{13,26,27}$]-hGRF(1-29)-NH$_2$;

[His$^1$, Ser$^{7,8,19}$, Ala$^{9,15,18,28}$, Orn$^{12}$, Arg$^{12,21}$, Leu$^{13,27}$, Val$^{26}$]-hGRF(1-29)-OH;

[Leu$^{5,13,26}$, Ser$^{7,19}$, Ala$^{9,18,28}$, Arg$^{12,21}$, Nle$^{27}$]-hGRF(1-29)-NH$_2$;

[His$^1$, Ser$^{7,19}$, Thr$^8$, Ala$^{9,15,18,28}$, Arg$^{21}$, Leu13,26,27]-hGRF(1-29)-NH$_2$;

[His$^1$, Ser$^{7,8,19}$, Ala$^{9,15,28}$, Arg$^{12,21}$, Leu$^{26,27}$]-hGRF(1-29)-NH$_2$;

[His$^1$, Ser$^{7,8,19}$, Ala$^{9,18,28}$, Arg$^{12,21}$, Ile$^{13}$ Leu$^{26,27}$]-hGRF(1-29)-NH$_2$;

[His$^1$, Tyr$^6$, Ser$^{7,8,19}$, Ala$^{9,15,18,28}$, Arg$^{12}$, Phe$^{13}$, Leu$^{26}$]-hGRF(1-29)-OH;

[D-Asp$^2$, Ser$^{7,8,19}$, Ala$^{9,15,18,28}$, Arg$^{12,21}$, Leu$^{13,26}$, Nle$^{27}$]-hGRF(1-29)-NH$_2$;

[D-Phe$^1$, Ser$^{7,8}$, Ala$^{9,15,28}$, Arg$^{12,21}$, Leu$^{13,26}$, Nva$^{27}$]-hGRF(1-29)-NH$_2$;

[D-His$^1$, D-Asp$^3$, Ser$^{7,19}$, Ala$^{9,15,18,28}$, Arg$^{12}$, Leu$^{13,26}$, Nle$^{27}$, Orn$^{21}$]-hGRF(1-29)-NH$_2$;

[N$^a$Me-D-Tyr$^1$, Ser$^{7,8,19}$, Ala$^{9,18,28}$, Orn$^{11}$, Arg$^{12,21}$, Leu$^{13,26}$, Ile$^{27}$]-hGRF(1-29)-NH$_2$;

and/or generally equivalent residues can be substituted for naturally occurring residues, as is known in the overall art of peptide chemistry, to produce other analogs having increased resistance to proteolysis, for example, and also having at least a substantial portion of the potency of the claimed polypeptide, without deviating from the scope of the invention, such as those set forth in Example IV. Likewise known substitutions in the carboxyl moiety at the C-terminus, e.g. a lower alkyl amide, also produce equivalent molecules.

Particular features of the invention are emphasized in the claims that follow.

What is claimed is:

1. A synthetic peptide having the sequence:
$R_1$-$R_2$-$R_3$-Ala-$R_5$-$R_6$-$R_7$-$R_8$-$R_9$-$R_{10}$-$R_{11}$-$R_{12}$-$R_{13}$-Leu-$R_{15}$-Gln-Leu-$R_{18}$-$R_{19}$-$R_{20}$-$R_{21}$-Leu-Leu-Gln-Glu-$R_{26}$-$R_{27}$-$R_{28}$-Arg-Y wherein $R_1$ is Tyr, D-Tyr, Met, Phe, D-Phe, Leu, His or D-His, which has either a $C^{\alpha}Me$ or $N^{\alpha}Me$ substitution or is unsubstituted; $R_2$ is Ala or D-Ala; $R_3$ is Asp or D-Asp; $R_5$ is Ile or Leu; $R_6$ is Phe or Tyr; $R_7$ is Ser or Thr; $R_8$ is Ser, Asn, Thr or Gln; $R_9$ is Ala or Ser; $R_{10}$ is Tyr, Phe or Leu; $R_{11}$ is Arg, Orn or Lys; $R_{12}$ is Arg, Orn or Lys; $R_{13}$ is Ile, Leu, Phe or Val; $R_{15}$ is Gly or Ala; $R_{18}$ is Ala or Ser; $R_{19}$ is Ser or Ala; $R_{20}$ is Arg, Orn or Lys; $R_{21}$ is Arg, Orn or Lys; $R_{26}$ is Leu, Ile, Val or Phe; $R_{27}$ is Nle, Nva, Gly, Ala, Val, Leu, Ile, Ser, Thr, Lys, Arg, Asp, Asn, Glu, Gln, Cys, Met, Phe, Tyr, Pro, Trp or His; $R_{28}$ is Ala, Leu Asn, Gln, or Ser; and Y is OH or $NH_2$; provided however that at least four of the residues contituting $R_5$, $R_6$, $R_7$, $R_8$, $R_9$, $R_{10}$, $R_{11}$, $R_{12}$, $R_{13}$, $R_{15}$, $R_{18}$, $R_{19}$, $R_{20}$, $R_{21}$, and $R_{26}$ are different from the residues appearing in that respective position in native hGRF and provided further that at least two of the following four residues are present: $R_9$ is Ala, $R_{18}$ Ala, $R_{19}$ is Ser and $R_{28}$ is Ala.

2. The peptide of claim 1 wherein $R_7$ is Ser.
3. The peptide of claim 1 wherein $R_9$ is Ala.
4. The peptide of claim 1 wherein $R_{12}$ is Arg.
5. The peptide of claim 1 wherein $R_{18}$ is Ala.
6. The peptide of claim 1 wherein $R_{13}$, $R_{26}$ and $R_{27}$ are Leu, $R_{28}$ is Ala and Y is OH.
7. The peptide of claim 1 wherein $R_{13}$ is Leu, $R_{26}$ is Leu, $R_{27}$ is Leu, $R_{28}$ is Ala and Y is $NH_2$.
8. The peptide of claim 1 wherein $R_{27}$ is Ile.
9. The peptide of claim 1 wherein $R_1$ is Tyr, $R_2$ is Ala and $R_3$ is Asp.
10. The peptide of claim 1 wherein $R_{19}$ is Ser.
11. The peptide of claim 1 wherein $R_7$ is Thr and $R_8$ is Gln.
12. The peptide of claim 1 where $R_{12}$ is Orn.
13. The peptide of claim 1 wherein $R_{21}$ is Arg.
14. The peptide of claim 1 wherein $R_5$ is Leu, $R_6$ is Phe, $R_{10}$ is Tyr, $R_{11}$ is Arg, $R_{20}$ is Arg and $R_{27}$ is Leu.
15. The peptide of claim 1 wherein $R_{13}$ is Leu, $R_{15}$ is Ala, $R_{26}$ is Val, $R_{27}$ is Leu and $R_{28}$ is Ala.
16. The peptide of claim 1 wherein $R_1$ is His, $R_2$ is Ala and $R_3$ is Asp.
17. The peptide of claim 1 having the formula: H-Tyr-Ala-Asp-Ala-Ile-Phe-Ser-Ser-Ala-Tyr-Arg-Arg-Leu-Leu-Ala-Gln-Leu-Ala-Ser-Arg-Arg-Leu-Leu-Gln-Glu-Leu-Leu-Ala-Arg-OH.
18. The peptide of claim 1 having the formula: H-Tyr-Ala-Asp-Ala-Ile-Phe-Ser-Ser-Ala-Tyr-Arg-Arg-Leu-Leu-Ala-Gln-Leu-Ala-Ser-Arg-Arg-Leu-Leu-Gln-Glu-Leu-Leu-Ala-Arg-$NH_2$.
19. A pharmaceutical composition for stimulating the release of GH in an animal comprising an effective amount of the peptide of claim 1 or a nontoxic salt thereof, and a pharmaceutically or veterinarily acceptable liquid or solid carrier therefor.
20. A method of stimulating the release of growth hormone in an animal, which comprises administering to said animal an effective amount of a synthetic peptide according to claim 1.

* * * * *

[Phe$^1$, Tyr$^6$, Ser$^{8,19}$, Ala$^{15,18,28}$, Arg$^{12,21}$, Leu$^{26,27}$]-hGRF(1-29)-NH$_2$;

[His$^1$, Ser$^{7,8}$, Ala$^{9,15,28}$, Arg$^{12}$, Leu$^{13,26,27}$, Orn$^{20,21}$]-hGRF(-29)-NH$_2$;

[Ser$^{7,8,19}$, Ala$^{9,15,18,28}$, Leu$^{10,13}$, Arg$^{12,21}$, Phe$^{26}$, Glu$^{27}$]-hGRF(1-29)-NH$_2$;

[C$^a$Me-Tyr$^1$, Ser$^{7,8,19}$, Ala$^{9,15,218,28}$, Arg$^{12,21}$, Leu$^{13,26}$, Orn$^{20}$, Asp$^{27}$]-hGRF(1-29)-NH$_2$;

[Leu$^{1,13}$, Ser$^{7,8,19}$, Ala$^{9,18,28}$, Arg$^{12,21}$, Ile$^{26,27}$]-hGRF(1-29)-OH;

[N$^a$Me-Met$^1$, Ser$^{7,19}$, Thr$^8$, Ala$^{9,15,18,28}$, Lys$^{11}$, Arg$^{12,21}$, Leu$^{13,26,27}$]-hGRF(1-29)-NH$_2$;

[Ser$^{7,8}$, Ala$^{9,15,18}$, Arg$^{12,21}$, Leu$^{13,26,27}$, Asn$^{28}$]-hGRF(1-29)-NH$_2$;

[N$^a$Me-His$^1$, Ser$^{7,8,19}$, Phe$^{10}$, Ala$^{15,18,28}$, Orn$^{12,21}$, Leu$^{13,26}$, Lys$^{20}$, Gln$^{27}$]-hGRF(1-29)-NH$_2$;

[C$^a$Me-His$^1$, Ser$^{7,19}$, Gln$^8$, Ala$^{9,15,18,28}$, Orn$^{11}$, Arg$^{12,21}$, Leu$^{13,26}$, Trp$^{27}$]-hGRF(1-29)-OH;

[His$^1$, Ser$^{7,8,19}$, Ala$^{9,15,18,28}$, Arg$^{12}$, Leu$^{13,26}$, Lys$^{20}$, Tyr$^{27}$]-hGRF(-29)-NH$_2$.

These analogs are judged to be substantially pure using TLC and HPLC.

These synthetic peptides, by comparison with synthetic hGRF(1-40)-OH, are found to exhibit at least about the same, and often greater, potencies for the secretion of GH.

As an example of testing the effectiveness of the synthetic peptide of Example I to promote the release of growth hormone, in vitro assays are carried out using synthetic hGRF(1-40)-OH as a standard in side-by-side comparison with equimolar concentrations of the various other analogs and fragments synthesized. Cultures are used which include cells of rat pituitary glands removed four days previous to testing. Cultures which are considered optimal for the secretion of growth hormone are used for the comparative testing, in the general manner described in Vale et al. *Endocrinology*, 91, 562–572 (1972) and as more particularly described in Vale et al., *Endocrinology*, 112, 1553–1555 (1983). Incubation with the substance to be tested is carried out for 4 hours, and aliquots of the culture medium are removed and processed to measure their respective content of immunoreactive GH(ir GH) by a well-characterized radioimmunoassay. The results of this comparative testing using equimolar concentrations show that the peptides of Examples I and II have a potency equivalent to the hpGRF(1-40)-OH standard.

Such synthetic hpGRF analogs should be useful for human applications in which a physician wishes to elevate GH production, and they should be preferred over native hpGRF. The solid-phase synthesis of these analogs is easier than the synthesis of the native molecule due to the shorter length of the hpGRF analog peptide. Furthermore, the more ordered structure found in the analogs may yield a more stable peptide, thus making it easier to purify. Stimulation of GH secretion by such analogs is of interest in patients with complete or relative GH deficiency caused by underproduction of endogenous GRF. Furthermore, it is probable that increased GH secretion and its attendant increase in growth could be obtained in humans or animals with normal GH levels. Moreover, administration should alter body fat content and modify other GH-dependent metabolic, immunologic and developmental processes. For example, these analogs may be useful as a means of stimulating anabolic processes in human beings under circumstances such as following the incurring of burns. As another example, these analogs may be administered to commercial warm-blooded animals, such as chickens, turkeys, pigs, goats, cattle and sheep, and may be used in aquaculture for raising fish and other cold-blooded marine animals, e.g. sea turtles and eels, and amphibians, to accelerate growth and increase the ratio of protein to fat gained by feeding effective amounts of the peptides.

For administration to humans, these synthetic peptides should have a purity of at least about 93% and preferably at least 98%. Purity, for purposes of this application, refers to the intended peptide constituting the stated weight % of all peptides and peptide fragments present. For the administration of such synthetic peptides to commercial and other animals in order to promote growth and reduce fat content, a purity as low as about 5%, or even as low as 0.01%, may be acceptable.

These synthetic peptides or the nontoxic salts thereof, combined with a pharmaceutically or veterinarily acceptable carrier to form a pharmaceutical composition, may be administered to animals, including humans, either intravenously, subcutaneously, intramuscularly, percutaneously, e.g. intranasally, or even orally. The administration may be employed by a physician to stimulate the release of GH where the host being treated requires such therapeutic treatment. The required dosage will vary with the particular condition being treated, with the severity of the condition and with the duration of desired treatment.

Such peptides are often administered in the form of nontoxic salts, such as acid addition salts or metal complexes, e.g., with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like. If the active ingredient is to be orally administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

The peptides should be administered to humans under the guidance of a physician, and pharmaceutical compositions will usually contain the peptide in conjunction with a conventional, solid or liquid, pharmaceutically-acceptable carrier. Usually, the parenteral dosage will be from about 100 nanograms to about 50 micrograms of the peptide per kilogram of the body weight of the host.

Although the invention has been described with regard to its preferred embodiments, particularly Examples I and II, which constitute the best mode presently known to the inventors, it should be understood that various changes and modifications as would be obvious to one having the ordinary skill in this art may be made without departing from the scope of the invention which is set forth in the claims appended hereto. For example, modifications in the peptide chain, particularly deletions of one or two residues beginning at the C-terminus of the peptide, can be made in accordance with known experimental practices to date to create peptides that retain very substantial portions of the biological potency of the peptide, and such peptides are considered as being within the scope of the invention. Moreover, additions may be made to the C-terminus,

UNITED STATES PATENT AND TRADEMARK OFFICE
CERTIFICATE OF CORRECTION

PATENT NO. : 4,689,318

DATED : August 25, 1987

INVENTOR(S) : Kaiser, et al.

It is certified that error appears in the above-identified patent and that said Letters Patent is hereby corrected as shown below:

Column 2, line 4, Change "R hd27" to --$R_{27}$--,

Column 2, line 60, Change "$X^1R_1$" to --$X^1-R_1$--.

Column 7, line 59, Change "0.46x≈cm" to --0.46 x 25 cm--.

Column 10, line 34, Change "Ser($H^4$) to --Ser($X^4$)--,

Column 10, line 36, Change "2ClZ" to --2Cl-Z--.

Column 12, line 53, Change "Leu13,26,27]" to --$Leu^{13,26,27}$]--.

Column 13, line 7, Change "$Ala^{9,15,218,28}$" to --$Ala^{9,15,18,28}$,--.

UNITED STATES PATENT AND TRADEMARK OFFICE
CERTIFICATE OF CORRECTION

PATENT NO. : 4,689,318

DATED : August 25, 1987

INVENTOR(S) : Kaiser, et al.

It is certified that error appears in the above-identified patent and that said Letters Patent is hereby corrected as shown below:

Column 15, line 29, Between "Leu" and "Asn" insert -- , -- (comma),

Column 15, line 36, After "$R_{18}$" insert --is--.

Signed and Sealed this

Fifth Day of April, 1988

Attest:

DONALD J. QUIGG

Attesting Officer

Commissioner of Patents and Trademarks